(12) United States Patent
Pugh

(10) Patent No.: US 11,651,705 B2
(45) Date of Patent: May 16, 2023

(54) TRACKING AND DIGITAL DOCUMENTATION OF HAPTIC MANIPULATION DATA USING WEARABLE SENSORS

(71) Applicant: Carla Marie Pugh, Menlo Park, CA (US)

(72) Inventor: Carla Marie Pugh, Menlo Park, CA (US)

( * ) Notice: Subject to any disclaimer, the term of this patent is extended or adjusted under 35 U.S.C. 154(b) by 142 days.

(21) Appl. No.: 16/791,016

(22) Filed: Feb. 14, 2020

(65) Prior Publication Data

US 2020/0184850 A1 Jun. 11, 2020

Related U.S. Application Data

(63) Continuation-in-part of application No. 15/683,450, filed on Aug. 22, 2017, now abandoned, which is a continuation of application No. 14/270,526, filed on May 6, 2014, now Pat. No. 9,741,264, which is a continuation-in-part of application No. 12/371,392, filed on Feb. 13, 2009, now Pat. No. 8,764,450.

(60) Provisional application No. 62/892,967, filed on Aug. 28, 2019, provisional application No. 61/029,202, filed on Feb. 15, 2008.

(51) Int. Cl.
*G09B 23/30* (2006.01)
*G09B 23/28* (2006.01)
*G06F 3/041* (2006.01)
*G16H 20/30* (2018.01)

(52) U.S. Cl.
CPC ............ *G09B 23/30* (2013.01); *G06F 3/0414* (2013.01); *G09B 23/288* (2013.01); *G16H 20/30* (2018.01)

(58) Field of Classification Search
CPC ...... G16H 20/30; G09B 23/28; G09B 23/281; G09B 23/288; G09B 23/30; G06F 3/04; G06F 3/0414
See application file for complete search history.

(56) References Cited

U.S. PATENT DOCUMENTS

| | | | | |
|---|---|---|---|---|
| 2004/0034394 | A1* | 2/2004 | Woods | A61N 1/37247 607/46 |
| 2008/0171311 | A1* | 7/2008 | Centen | G09B 23/288 601/41 |
| 2010/0167248 | A1* | 7/2010 | Ryan | A61B 34/76 434/262 |
| 2015/0145682 | A1* | 5/2015 | Harris | G06F 3/014 340/573.1 |
| 2019/0206134 | A1* | 7/2019 | Devam | G06F 3/011 |

(Continued)

FOREIGN PATENT DOCUMENTS

| | | | | |
|---|---|---|---|---|
| CN | 202654114 U | * | 1/2013 | ............. G16H 20/90 |
| WO | WO-03105059 A1 | * | 12/2003 | ............. A61H 33/60 |
| WO | WO-2020003130 A1 | * | 1/2020 | ......... A61B 5/02055 |

*Primary Examiner* — Timothy A Musselman
(74) *Attorney, Agent, or Firm* — Lumen Patent Firm

(57) ABSTRACT

A method and system are provided for tracking manipulation data. A wearable sensor array is capable of providing force data, motion data and location data. A body part of a person is covered with the wearable sensor array. The body part of the person is being manipulated through the wearable sensor array, and then a computer system obtains sensor data from the wearable sensor array. The computer system generates a force, motion and location map based on the obtained sensor data which is useful for a variety of purposes as detailed herein.

10 Claims, 1 Drawing Sheet

(56) References Cited

U.S. PATENT DOCUMENTS

2020/0126297 A1\* 4/2020 Tian .......................... G06T 7/55
2021/0020069 A1\* 1/2021 Komala ................. G09B 23/30

\* cited by examiner

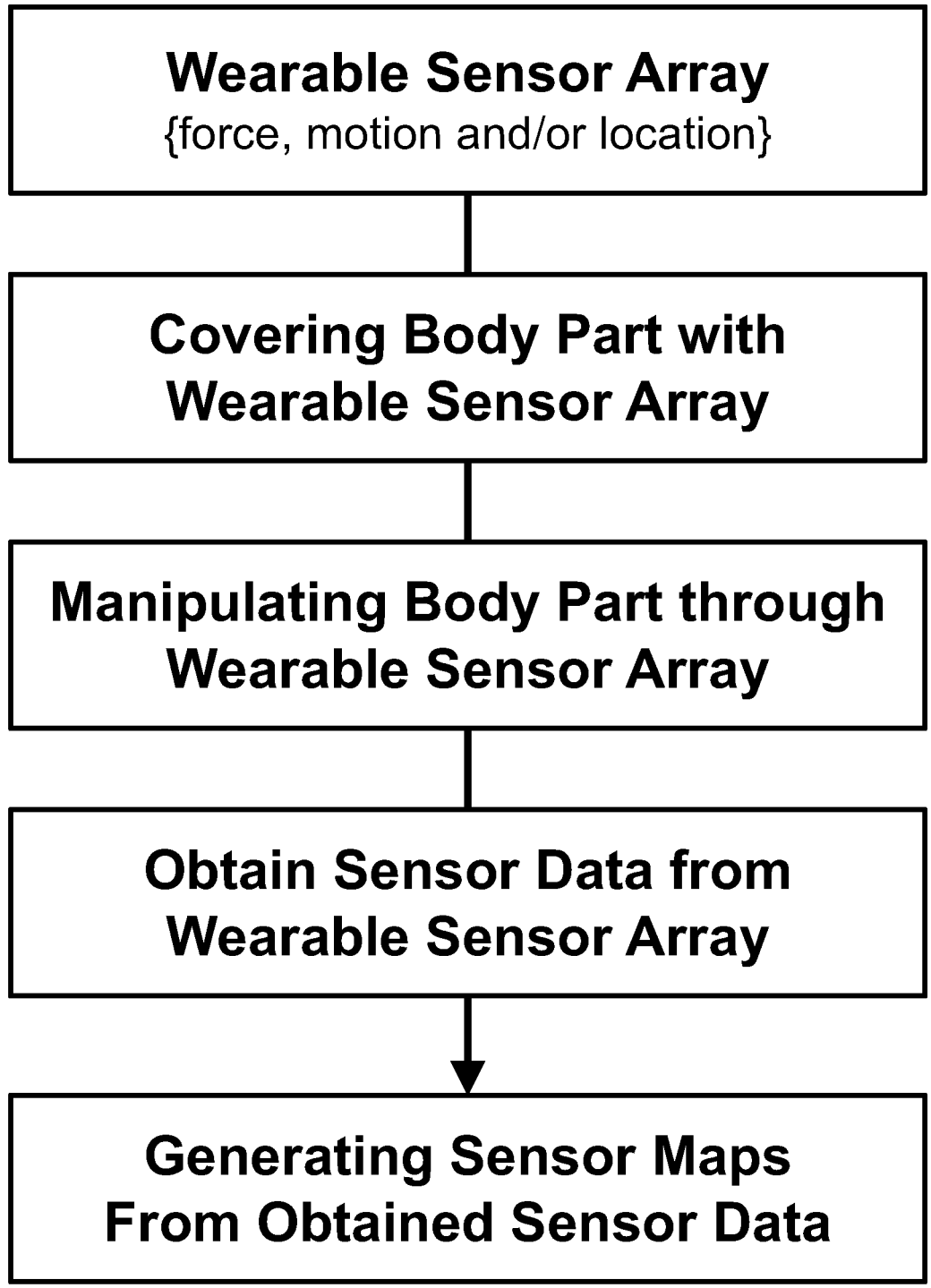

TRACKING AND DIGITAL DOCUMENTATION OF HAPTIC MANIPULATION DATA USING WEARABLE SENSORS

CROSS-REFERENCE TO RELATED APPLICATIONS

This application claims priority from U.S. Provisional Patent Application 62/892,967 filed Aug. 28, 2019, which is incorporated herein by reference.

This application is a continuation-in-part of U.S. patent application Ser. No. 15/683,450 filed Aug. 22, 2017, which is incorporated herein by reference.

U.S. patent application Ser. No. 15/683,450 is a continuation of U.S. patent application Ser. No. 14/270,526 filed May 6, 2014, which is incorporated herein by reference.

U.S. patent application Ser. No. 14/270,526 filed May 6, 2014 is a continuation-in-part of U.S. patent application Ser. No. 12/371,392 filed Feb. 13, 2009, which is incorporated herein by reference.

U.S. patent application Ser. No. 12/371,392 filed Feb. 13, 2009 claims the benefit of U.S. Provisional Application 61/029,202 filed Feb. 15, 2008, which is incorporated herein by reference.

FIELD OF THE INVENTION

This invention relates to tracking manipulation data using wearable sensors during a medical procedure, a diagnostic or therapy session or a massage.

BACKGROUND OF THE INVENTION

Healthcare providers could benefit from sensors and sensor-enabled tools that can be used for capturing, quantifying, characterizing, and displaying hands-on maneuvers in a standardized, digital format. Digital documentation of hands-on medical examinations and procedures allows for a standardized method of communication and data sharing both for improving the understanding of clinical disease and the hands-on skills necessary to diagnose and treat disease. Data generated from said sensors or sensor-enabled tools would be used to indicate specialized routines, preferences or idiosyncrasies as well as confirmation of the utility of standardized approaches. As digital documentation of haptic or hands-on maneuvers is not in current use in healthcare this technique can also be used for clarification and standardization of evidenced based recommendations which are currently either verbalized or in written format.

Similarly, massage therapists, chiropractors or other professionals who use therapeutic or diagnostic touch could also benefit from sensors and sensor-enabled tools that can be used for capturing, quantifying, characterizing, and displaying hands-on maneuvers in a standardized, digital format. Digital documentation of hands-on therapeutic or diagnostic examinations and procedures also allows for new communication methods and data sharing. As many of the patients seeking these services are awake and have their own preferences and personalized outcomes, digital documentation can serve as an important, real-time communication tool. This also applies to awake patients for medical examinations and procedures where there is an opportunity to align patient preferences with the standard of care.

Digital documentation of hands-on maneuvers can allow for the creation of client preference profiles for future sessions as well as inter-session comparisons or the like. For clinical procedures and exams, the digital approach could lead to auto documentation, comparison and digital diagnosis using pattern recognition to detect changes patient tolerance and perception as well as differences in practitioner perception and approach. The recorded information would not only represent practitioner workflow and preferences but would also represent organ mobility and pliability hence a haptic and digital representation of anatomical and pathological variations in human anatomy. For clinical and therapeutic touch, such technology could lead to the real-time feedback or sharing on preferred techniques, as well as quantitative feedback regarding the speed, depth and sequence of tissue or anatomical manipulation of various body parts or organs.

No formalized methods or technology tools exist to facilitate digital documentation of haptic manipulations in medicine and surgery. During a medical procedure or examination, a series of technical, cognitive and perceptual events and decisions take place, many of which are not visible, nor can they be tracked by the human observer. Moreover, these technical, cognitive and perceptual events are difficult to explain verbally. For example, an orthopedic surgeon using his or her hands to assess and reduce a fracture is consciously and subconsciously "feeling" for the tension and relationship between the bones and muscles, while also timing their manipulations in such a way to minimize the patient's counter-response to their planned anatomical manipulation. Only parts of this complex interaction between the sense of touch, sight, perception and hearing can be seen by an observer. Moreover, a verbal account of these sensory inputs, motor outputs and actions are guaranteed to be woefully inadequate and insufficient in detail for training purposes or clinical documentation. Similarly, a surgeon in the operating room performing open, laparoscopic or robotic surgery will have a similar mix of touch, visual and perceptual experiences that define the relationship between the surgeon's hands, instruments and patients' organs. Here too, a verbal account of these sensory inputs, motor outputs and actions are guaranteed to be woefully inadequate and insufficient in detail for training purposes or clinical documentation. As such, digital documentation would create a new modality and language for documenting haptic manipulations. Digital documentation would also enable cross-talk and new communication pathways for healthcare providers and patients Similarly, when considering diagnostic and therapeutic touch such as massage or chiropractic treatments, no formalized methods and technology tools exist to facilitate the customer's ability to indicate haptic or touch preferences during hands-on anatomical manipulations.

There is a need for customer-initiated training and assessment of surgical and/or therapy interactions, particularly training to optimize the sense of touch. In essence, the customer can "train" the therapist on the customer's touch preferences. During a customer-therapist exchange, technical criteria such as "sequence of touch" and "depth" or "completeness of strokes", traditionally represent techniques that rely primarily on declarative and procedural knowledge but do not take customer preferences into consideration. Other aspects of the touch routine such as strategic force combinations or serial progression from one muscle group to another are also important as this provides systematic and therapeutic relaxation while increasing circulation and blood flow. In addition, although these techniques are relatively universal not all of them can be assessed or verbally communicated in an objective fashion that will routinely yield the perfect customer experience, as such, a technology tool that enhances communication capabilities for haptic interactions is desperately needed.

Anecdotally, some practitioners are reported to simply have "good touch" or "good pair of hands". Despite the importance of this innate skill within hands-on professions, no formalized methods or tools exist to objectively and quantitatively assess, communicate or define the preferred range of haptic skills desired of practitioners during the hiring process, initial training, or throughout their professional careers. As touch, dexterity and other haptic related psychomotor skills are extremely difficult to learn by observation alone, methods for providing digital documentation and communication of these skills are necessary. Haptic training and testing are the only way to ensure high quality therapeutic and diagnostic interactions and anatomical manipulations. Thus, sensors, sensor-enabled tools and visual displays that enhance digital documentation and communication of these skills as well as training of therapists/practitioners and trainees are desperately needed.

SUMMARY OF THE INVENTION

This invention specifically addresses a need for sensors and sensor-based technology tools to:
1) enable the acquisition of objective data to quantify various touch, medical and surgical procedure techniques,
2) support data analytics to characterize, model and compare optimal techniques (based on expert data) and techniques used by novice or intermediate level practitioners, and
3) to allow multi-directional feedback and personal requests including from patients to doctors, customers to therapists and doctor to doctor for example and
4) multi-directional feedback displays can also facilitate relevant cues, guidance and feedback to users for training and assessment purposes.

For example, a sensor-enabled tool could collect and analyze data from multiple experts to develop models of optimal techniques. Data visualization allows experts to share tips and tricks and facilitates even greater expertise and significant improvements the quality of hands-on procedures, exams and therapeutic touch. In addition, novice and intermediate practitioners and therapists could also use the same system to collect their own data and compare it to a database of experts or highly rated practitioners. Expert data could also be displayed in real-time as an expert demonstrates a technique, allowing a trainee or another expert with a different approach to see the data associated with technical mastery. In addition, expert data could be displayed to a novice as a form of guidance while the novice attempts to replicate the same methods and associated forces or motion patterns to achieve a specific anatomic manipulation. Likewise, therapist's data could be displayed to a customer, real time, during an anatomic manipulation such as a massage, and said customer could use such data to communicate personal preferences and "train" the therapist. Data collected in an initial training or information exchange context could be used by both instructors and trainees to accurately assess a novice therapist/practitioners' skills, identify areas in need of improvement, and provide targeted instruction/feedback to optimize skill acquisition and customer interactions. The same system could be used by practitioners throughout their training and career continuums, allowing them to continually assess and hone their skills over time a part of a self-assessment process.

A benefit of the embodiments of this invention is the use of wearable technology to automate clinical documentation in the Electronic Health Record which can greatly facilitate documentation accuracy and provide more clinical and anatomical detail than direct human entry via typing or verbal dictation.

In one embodiment, the invention is a method or system for tracking manipulation data, which includes the steps of:
(a) having a wearable sensor array capable of providing force data, motion data and location data;
(b) covering a body part of a person with the wearable sensor array;
(c) manipulating the body part of the person through the wearable sensor array;
(d) a computer system obtaining sensor data from the wearable sensor array; and
(e) the computer system generating a force, motion and location map based on the obtained sensor data.

The force, motion and location map could be stored in a database.

Embodiments could further use an imaging or magnetic motion device to track the hand motion of a person performing the manipulation process.

Embodiments could further include the person receiving the manipulation providing feedback to the computer system regarding the manipulation process and the computer system adding and synchronizing this person's feedback to the force, motion and location map in time.

The manipulating step could be a medical exam, a medical procedure, a therapy session or a massage. The manipulating step could be a direct or an indirect manipulation.

BRIEF DESCRIPTION OF THE DRAWINGS

FIG. 1 shows the method or system for tracking manipulation data according to an embodiment of the invention.

DETAILED DESCRIPTION

FIG. 1 shows the method and system for tracking manipulation data. A wearable sensor array is capable of providing force data, motion data and location data. A body part of a person is covered with the wearable sensor array. The body part of the person is being manipulated through the wearable sensor array, and then a computer system obtains sensor data from the wearable sensor array. The computer system generates a force, motion and location map based on the obtained sensor data which is useful for a variety of purposes as detailed herein.

A typical operating room (1a) is depicted in FIG. 1 and referenced in U.S. Provisional Patent Application 62/892, 967 filed Aug. 28, 2019, which is incorporated herein by reference. Expert surgeon (1b) is manipulating a laparoscopic instrument while data is being collected from a wearable sensor array on both of her hands (1c). In addition, her colleague, expert surgeon (1d), is also wearing said wearable sensors on both of his hands (1c). As surgeon (1b) and surgeon (1d) perform an operation on the patient (1e), they are able to share manipulation data (1f) relating to their preferred technical approach. Said data could be displayed on an overhead monitor (1g) or a sterile monitor in the operative field (1h). In one embodiment, said data is displayed real-time over the operative anatomy of the patient (1e) or on an operative video (1i). In another embodiment, said manipulation data can be displayed independent of operative video (1i) on a cell phone (1j) or tablet (1k). Each user desiring access to the manipulation data (1f) can decide how to view the data. Viewing manipulation data in synchronization with surgical video (1l) enables anatomical location data to be visualized directly. Without surgical video in the background, anatomical location data (1m) can be indicated on the screen. In addition to expert surgeon (1b) and expert surgeon (1d) sharing operative tips and tricks while donning the wearable sensors, novice surgeon (1n) can also learn by observing their manipulation data in the operating room via surgical displays (1g, 1h) or after the operation via cellphone (1j), tablet (1k) or other display device.

Said wearable sensors are depicted in FIG. 2 and referenced in U.S. Provisional Patent Application 62/892,967 filed Aug. 28, 2019, which is incorporated herein by reference. Said wearable sensors can track motion (2a), force 2b, 2c, 2d and location 2a, 2b, 2c, 2d. The motion sensors can be optical or magnetic or any combination of materials that allow movement tracking. The force sensors can be made of any engineering or chemical components including ultrathin, flexible electronics mounted onto or mixed within silicon or other materials used to make artificial skin, adhesives or surgical gloves. Anyone skilled in the art of wearable sensor technology could define a sensor possible for use in the manipulation data system. Specific sensor requirements depend on the medical examination or procedure and include individual or combined sensor arrays capable of providing force, motion or location data or a combination of these types of data outputs.

Said arrays should include at least two sensors for each hand. The sensor could be placed in any location however, certain positions such as the index finger, thumb or wrist are known to collect the highest quality manipulation data as these locations are the most common actuators of force and motion. In the case of a single sensor per digit or other hand location, basic hand and finger location information can be obtained by indicating designated sensor numbers. For example, sensor 1 (2e) could always be used to indicate the thumb location whereas sensor 2 (2f) could always be used to indicate the index finger location. In the case of multiple, visually discrete or microscopic sensors (2g) per digit (2b, 2c) or other hand location (2d), more detailed information can be determined regarding what part of the finger or hand location was used at each moment during an examination or procedure.

FIG. 3 as referenced in U.S. Provisional Patent Application 62/892,967 filed Aug. 28, 2019, which is incorporated herein by reference, depicts an example of less than one minute of surgical manipulation data for the left (3a) and right (3b) hand of a cardiothoracic surgeon. The video image in the center shows the surgeon (3c) with a pair of forceps (3d) in his left hand (3e) and a needle driver (3f) in his right hand (3g). The surgeon is sewing the atrial appendage (3h) of a bovine heart (3i) placed in a simulated chest cavity (3j). The manipulation data for the left hand (3a) has a small area with mostly a linear pattern indicating that the left hand (3e) took multiple, small movements from left to right and right to left to grasp either the needle from the needle driver (3f) or the atrial appendage (3h) tissue. The manipulation data for the right hand (3b) has a larger area. In one part of the manipulation data, there is a large, repeating loop-like or circular pattern (3k) that occurs three times. These three loops are created by the motion of the surgeon's right hand (3g) when pulling the suture thread through the atrial appendage (3h) tissue after each stitch. The surgeon does not put the needle driver (3f) down or reach for the mayo stand after placing each stitch. These movements would have generated a different pattern in the manipulation motion data. However, during one of the looped motions (3k) there is a slightly different pattern noted.

Specifically, in the middle loop, there is a downward dip (3l) in the loop pattern near the top of the loop on the left side. This pattern was generated as the surgeon had to move the suture in a slightly different pattern to get it untangled from the inferior edge of the atrial appendage (3h).

When using the manipulation data to compare technique, FIG. 4 as referenced in U.S. Provisional Patent Application 62/892,967 filed Aug. 28, 2019, which is incorporated herein by reference, differences can be seen from a variety of perspectives. When comparing the righthand manipulation data (4a) of a junior surgeon with the righthand manipulation data (4b) of a senior surgeon one can see that the senior surgeon has a simpler pattern that takes on the shape of a backwards letter "C". While the junior surgeon does have a similar pattern, the motion lines are more diverse and less predictable. Also, the senior surgeon spends more time in one area near the bottom of the backwards letter "C" (4c).

Additional information can be had when looking at the manipulation data of the left hands of both surgeons. The left-hand manipulation data (4d) of the senior surgeon appears to have a longer path length compared to the lefthand manipulation data of the junior surgeon (4e). When considering the left- and righthand manipulation data together, it appears that the senior surgeon is more adept or ambidextrous during this part of the procedure and uses the left hand (4d) to assist the right hand (4b) in conducting a smoother performance compared to the junior surgeon's right hand (4a). It is also noted that the senior surgeon slows down (dark areas) within area (4c) more than the junior surgeon. In our prior work we have noted that the dark areas are where more of the important decisions are being made.

The benefits of storage and access to manipulation data cannot be overstated. However, in order for manipulation data to be useful, it has to be intuitive, easy to use and bring value to the current process of information storage and access. Currently, the Gold Standard method for documenting the surgical process is verbal dictation. Use of this format is woefully inadequate in the level of detail and more importantly lacks a basic level of standardization that would allow it to be useful for outcomes research or empirical investigations of best practices.

FIG. 5, as referenced in U.S. Provisional Patent Application 62/892,967 filed Aug. 28, 2019, which is incorporated herein by reference, outlines a process where sensors at the point of care (5a) can be used to capture and digitize the surgical process (5b). Sensor outputs must be processed to improve utility. Data reduction and visualization using various algorithms such as deep learning, image processing, dashboards and leaderboard display strategies are a critical step (5c). The electronic record is a perfect example where processed sensor data of surgical manipulations could benefit the current, text-based documentation (5d). Automating this process would greatly enhance the clinical workflow by decreasing Electronic Health Record charting times and improving the quality of that exists in the Electronic Health Record.

The concept of tracking and digital documentation of haptic manipulation data using wearable sensors extends well beyond the operating room. Physical examinations, bedside procedures, radiologic procedures and even outpatient office procedures and biopsies are all amenable to this process. The clinical breast examination provides a great example, as shown FIG. 6 and referenced in U.S. Provisional Patent Application 62/892,967 filed Aug. 28, 2019, which is incorporated herein by reference. In one of our early studies, we built a prototype of a wearable bra made of piezoelectric fabric (6a) that was capable of generating an accurate force profile of the two, previously identified stages of the clinical breast examination—"searching" and "palpating" (6*b*). The force profile for "searching" consists of an average force of 15-20 Newtons (6*c*) and narrow peak deflections (6*c*). The force profile for "palpating" a mass reaches higher forces (>30 Newtons) in the initial mass localization period (6*d*). In addition, the palpating phase is characterized by wider peaks (6*e*). Breast density and mass location also determine the force ranges. The current gold standard for documenting clinical breast examination findings is either via dictations, paper documents or computer-based forms (6*f*). Unfortunately, these forms represent an over processed version of the palpatory breast tissue exploration and does not capture certain information. During an examination performed by the healthcare practitioner, it is not uncommon to say the exam was normal as the final assessment when there may have been two or three areas where more time was spent due to dense or questionable tissue. Many practitioners do not document their full experience. Adding a wearable sensor to this process allows a fast, efficient and automated way of documenting the full palpatory experience. A pixel based heatmap of the forces (6*g*) generated during the exam could document the examination in more detail. For example, the practitioner may only note that there was abnormal thickening or potentially a mass in region II but may not mention that they spent more time and pressed harder in region III and IV before concluding these areas were normal. Another possibility with wearable sensors is the ability to display past examinations in series for comparison (6*h*). In addition, lay persons could be taught the self-examination (6*i*) and compare their examination technique and findings with that of their practitioner (6*j*) or a database of practitioners (6*k*).

The thyroid examination may be conducted using one's hands and or an ultrasound. Similar to the breast examination, a wearable sensor can capture the examination, FIG. 7 as referenced in U.S. Provisional Patent Application 62/892,967 filed Aug. 28, 2019, which is incorporated herein by reference. In another pilot study we used a wearable piezo fabric sensor (7*a*) to quantify the thyroid examination (7*b*). The sensor had eight total sensing areas including four on the left and four on the right (7*c*). The sensors were placed near the hyoid bone (sensor level 1), the thyroid cartilage area (sensor level 2), the cricoid and superior thyroid gland area (sensor level 3), and the inferior thyroid gland and sternal notch area (sensor level 4). These eight sensors revealed for the first time a digital pattern uniquely representative of a complete thyroid examination (7*b*).

Part A represents the point at which the clinician places their hands on the patient's neck and locates the appropriate anatomy (7*d*). Part B represents the practitioner asking the patient to swallow as the press more firmly on the left side of the neck (7*e*). Part C represents the practitioner asking the patient to swallow as the press more firmly on the right side of the neck (7*f*). This type of data could allow for confirmation of a complete examination as well as standardization of the forces needed for an accurate, evidence-based examination. Similarly, this same process could be used for ultrasound examination of the thyroid examination.

Clubfoot assessment and casting provides yet another example of a physical exam and treatment regimen that could benefit greatly from digital documentation of procedural manipulation data, FIG. 8 as referenced in U.S. Provisional Patent Application 62/892,967 filed Aug. 28, 2019, which is incorporated herein by reference. The current gold standard for documenting the physical examination and clinical assessment of a clubfoot baby is a checklist-based system called the Pirani Scoring system (8*a*). This system requires several steps, many of which are based on palpation forces such as checking the rigidity of equinous (8*b*), feeling the lateral part of the head of the talus (8*c*), and feeling the heel (8*d*). Although the scoring system has helped to provide a structured way of assessing a clubfoot baby, because it is largely based on subjective measures of touch and palpation forces, there may be a wide variation in clinical documentation, treatment and outcomes for the patients. In our prior work, we have used a variety of sensors including magnetic motion sensors under physicians' gloves (8*e*) and fabric-based sensors sewn directly onto the casting stockinette (8*f*) to quantify the exact amount of force applied during the clubfoot assessment (8*g*) and casting process (8*h*). As in other examinations at least two motion sensors are used (one for each hand) and two fabric-based sensors (one over the talus and one near the heel).

Using sensor technology to quantify the manipulation and casting forces allows for objective and standardized metrics for understanding and documenting this childhood disease in the electronic medical record (8*i*). This process will greatly facilitate clinical research by eliminating the subjective, physician-based documentation that currently exists.

In addition to surgical procedures and medical examinations, non-clinical, therapeutic manipulations would also benefit from digital documentation and data capture to facilitate communication, FIG. 9 as referenced in U.S. Provisional Patent Application 62/892,967 filed Aug. 28, 2019, which is incorporated herein by reference. Use of an ultrathin, sensor array (9*a*) capable of distinguishing anatomical massage landmarks would enable a massage therapist (9*b*) to adjust the depth, frequency and direction of their hands-on manipulation of various body parts based on verbal feedback or confirmation by the customer (9*c*). In addition, another option for improving communication during massage is for the customer (9*c*) to point to a screen (9*d*) indicating the preferred areas for specific manipulation. The customers screen (9*d*) could be shared with video or VR glasses (9*e*) or a larger room screen (9*f*). In addition, the wireless sensor (9*a*) could communicate directly with the VR glasses (9*e*) or screens (9*d*,9*f*). As both massage tables (9*g*) and massage chairs (9*h*) both have face holes (9*i*), this type of communication is greatly facilitated by customer visualization of massage palpation data on a screen (9*d*, 9*f*). For example, the red (9*j*) and yellow (9*k*) areas on the screens (9*d*, 9*f*) could indicate the areas the client prefers the deepest massage. Digitally recorded sessions and aggregated client profiles could be used to provide guidance to massage therapists just prior to and during subsequent sessions with the same client.

FIG. 10 as referenced in U.S. Provisional Patent Application 62/892,967 filed Aug. 28, 2019, which is incorporated herein by reference, summarizes the method for sensor-enabled massage communication and digital documentation. The client (10*a*) may input directly into a computer (10*b*) or database that feeds into a practitioner or massage therapist display (10*c*) or back to the client through a client display (10*d*). Likewise, a sensor overlay (10*e*) can store real-time or historical information on a computer (10*b*) that the client or practitioner may respond to through each of their respective displays (10*d*, 10*c*).

FIG. 11 as referenced in U.S. Provisional Patent Application 62/892,967 filed Aug. 28, 2019, which is incorporated herein by reference, summarizes the method for sensor-enabled medical communication and digital documentation. The surgeon or medical practitioner (11*a*) exerts movements and forces during the course of anatomical manipulations (11b) either with their hands or surgical instruments and generates manipulation data (11c). Said manipulation data (11c) can either be displayed real-time (11d) to facilitate communication or training with other medical practitioners (11a) or stored in a database (11e) or medical record for future communication or training use or clinical research. Both physician factors (11f) and patient factors (11g) independently effect the manipulation data (11c). For example, an inexperienced practitioner (11a) may yield manipulation data (11c) that represents specific MD factors (11f) in the manipulation data (11c) that may indicate specific technical deficiencies for example. Likewise, patient factors (11g) may demand specific surgical manipulations. In this instance, the manipulation data (11c) may help to characterize what it takes to alleviate specific disease processes. For example, in a patient with dense adhesions the surgeon may need to use multiple, short bursts of movement with high frequency but low velocity hence, the medical practitioner (11a) will generate manipulation data (11c) because of the dense adhesions, a specific patient factor (11g).

The manipulation data has additional benefits beyond digital documentation and communication. FIG. 12 as referenced in U.S. Provisional Patent Application 62/892,967 filed Aug. 28, 2019, which is incorporated herein by reference, shows how digital manipulation data (12a) can be used to expedite the review of video for personal learning or coaching. A major abdominal operation is used as an example. This operation yielded four hours of operative video and digital manipulation data (12a). Instead of looking at four hours of video, specific areas of the motion/manipulation data (12a) can be targeted. For example, the first target chosen is an unexpected segment of motion (12b). Because the motion data is synchronized with the video data, if one clicks or hovers over the targeted motion area (12b), then they will be directed to video segment 15 (12c) which shows the surgeon in the process of cauterizing some recently ligated tissue. The second target chosen is a segment of motion (12d) that is expected for this procedure. Hovering over this motion segment (12d) will reveal video segment 47 (12e) which shows routine dissection. Other data types could also be synchronized with digital manipulation data including audio data (12f), cognitive data (12g) and practitioner physiologic data (12h). Any combination of these data streams can be used to identify surgeon or practitioner factors that effects patient outcomes. Our prior work has shown that surgeons who have an accurate and efficient surgical protocol with excellent outcomes have similar motion patterns that generated that same digital manipulation data (12a). In addition, these surgeons demonstrate significantly higher use of team language in their audio data (12f); significantly higher use of executive function and lower cognitive load in their cognitive data (12g) as well as low physiologic parameters (12h).

What is claimed is:

1. A method of tracking manipulation data, comprising:
   (a) having a wearable sensor array capable of providing force data and location data;
   (b) covering a body part with the wearable sensor array;
   (c) a computer system obtaining sensor data from the wearable sensor array while the body part is being manipulated;
   (d) the computer system generating a force and location map based on the obtained sensor data;
   (e) a person receiving the manipulation providing force and location feedback to the computer system, wherein the force and location feedback is feedback other than the obtained sensor data; and
   (f) adding and synchronizing the person's force and location feedback to the force and location map in time.

2. The method as set forth in claim 1, wherein the force and location map are stored in a database.

3. The method as set forth in claim 1, further comprising using an imaging or magnetic motion device to track a hand motion of a person performing a manipulation process.

4. The method as set forth in claim 1, wherein the manipulating step is a medical exam, a medical procedure, a therapy session or a massage.

5. The method as set forth in claim 1, wherein the manipulating step is a direct or an indirect manipulation.

6. The method as set forth in claim 1, having a wearable sensor array capable of further providing motion data.

7. The method as set forth in claim 1, the computer system further generates a motion map.

8. The method as set forth in claim 7, wherein the motion map is stored in a database.

9. The method as set forth in claim 7, further comprising adding and synchronizing the person's force and location feedback to the motion map in time.

10. The method as set forth in claim 1, wherein the manipulating the body part is through the wearable sensor array.

* * * * *